United States Patent
Poon et al.

(10) Patent No.: US 10,828,502 B2
(45) Date of Patent: Nov. 10, 2020

(54) METHODS AND APPARATUS FOR POWER CONVERSION AND DATA TRANSMISSION IN IMPLANTABLE SENSORS, STIMULATORS, AND ACTUATORS

(71) Applicant: THE BOARD OF TRUSTEES OF THE LELAND STANFORD JUNIOR UNIVERSITY, Stanford, CA (US)

(72) Inventors: Ada Shuk Yan Poon, Redwood City, CA (US); Alexander J. Yeh, Palo Alto, CA (US)

(73) Assignee: THE BOARD OF TRUSTEES OF THE LELAND STANFORD JUNIOR UNIVERSITY, Stanford, CA (US)

( * ) Notice: Subject to any disclaimer, the term of this patent is extended or adjusted under 35 U.S.C. 154(b) by 0 days.

(21) Appl. No.: 16/013,513

(22) Filed: Jun. 20, 2018

(65) Prior Publication Data

US 2018/0296849 A1    Oct. 18, 2018

Related U.S. Application Data

(63) Continuation of application No. 14/637,148, filed on Mar. 3, 2015, now Pat. No. 10,004,913.
(Continued)

(51) Int. Cl.
*H02M 7/00* (2006.01)
*A61N 1/40* (2006.01)
(Continued)

(52) U.S. Cl.
CPC .............. *A61N 1/40* (2013.01); *H02J 7/025* (2013.01); *H02J 50/10* (2016.02); *H02J 50/40* (2016.02);
(Continued)

(58) Field of Classification Search
CPC ......... A61N 1/40; A61N 1/3787; H02J 7/025; H02J 50/80; H02J 50/40; H02J 50/10; H02J 5/005; Y10T 307/344; Y10T 307/406
See application file for complete search history.

(56) References Cited

U.S. PATENT DOCUMENTS 3,902,501 A    9/1975    Citron et al.
3,939,843 A    2/1976    Smyth
(Continued)

FOREIGN PATENT DOCUMENTS

WO    WO2009/008932 A2    1/2009
WO    WO2011/150430 A2    12/2011
(Continued)

OTHER PUBLICATIONS

Liou et al.; Wireless charging system of mobile handset using metamaterials-based cavity resonator; In Microwave Symposium Digest (MTT); 2012 MTT-S International; IEEE; 3 pages; Jun. 2012.
(Continued)

*Primary Examiner* — Kenneth B Wells
(74) *Attorney, Agent, or Firm* — Shay Glenn LLP

(57) ABSTRACT

Implantable devices and/or sensors can be wirelessly powered by controlling and propagating electromagnetic waves in a patient's tissue. Such implantable devices/sensors can be implanted at target locations in a patient, to stimulate areas such as the heart, brain, spinal cord, or muscle tissue, and/or to sense biological, physiological, chemical attributes of the blood, tissue, and other patient parameters. In some embodiments, the implantable devices can include power management schemes that have one or more AC-DC conversion chains arranged and configured to rectify the
(Continued)

induced alternating current or voltage into one or more energy domains. Methods of use are also described.

18 Claims, 12 Drawing Sheets

Related U.S. Application Data

(60) Provisional application No. 61/947,240, filed on Mar. 3, 2014.

(51) Int. Cl.
| | |
|---|---|
| *H02J 7/02* | (2016.01) |
| *H02J 50/10* | (2016.01) |
| *H02J 50/40* | (2016.01) |
| *H02J 50/80* | (2016.01) |
| *A61N 1/378* | (2006.01) |

(52) U.S. Cl.
CPC ............ *H02J 50/80* (2016.02); *A61N 1/3787* (2013.01); *Y10T 307/344* (2015.04); *Y10T 307/406* (2015.04)

(56) References Cited

U.S. PATENT DOCUMENTS

| | | | |
|---|---|---|---|
| 4,033,357 A | 7/1977 | Helland et al. | |
| 4,236,529 A | 12/1980 | Little | |
| 4,262,678 A | 4/1981 | Stokes | |
| 4,269,198 A | 5/1981 | Stokes | |
| 4,301,815 A | 11/1981 | Doring | |
| 4,407,303 A | 10/1983 | Akerstrom | |
| 4,409,994 A | 10/1983 | Doring | |
| 4,506,679 A | 3/1985 | Mann | |
| 4,582,069 A | 4/1986 | McArthur | |
| 4,592,356 A | 6/1986 | Gutierrez | |
| 4,658,835 A | 4/1987 | Pohndorf | |
| 4,716,888 A | 1/1988 | Wesner | |
| 4,721,118 A | 1/1988 | Harris | |
| 4,796,643 A | 1/1989 | Nakazawa et al. | |
| 4,841,971 A | 6/1989 | Hess | |
| 4,883,070 A | 11/1989 | Hanson | |
| 4,945,922 A | 8/1990 | van Krieken | |
| 4,957,118 A | 9/1990 | Erlebacher | |
| 5,193,539 A | 3/1993 | Schulman et al. | |
| 5,257,634 A | 11/1993 | Kroll | |
| 5,282,845 A | 2/1994 | Bush et al. | |
| 5,300,107 A | 4/1994 | Stokes et al. | |
| 5,358,514 A | 10/1994 | Schulman et al. | |
| 5,545,206 A | 8/1996 | Carson | |
| 5,662,697 A | 9/1997 | Li et al. | |
| 5,814,089 A | 9/1998 | Stokes et al. | |
| 5,833,603 A | 11/1998 | Kovacs et al. | |
| 5,868,741 A | 2/1999 | Chia et al. | |
| 5,908,433 A | 6/1999 | Eager et al. | |
| 5,953,223 A * | 9/1999 | Kato .................. | G03G 15/2003 363/37 |
| 5,957,965 A | 9/1999 | Moumane et al. | |
| 6,021,354 A | 2/2000 | Warman et al. | |
| 6,141,588 A | 10/2000 | Cox et al. | |
| 6,164,284 A | 12/2000 | Schulman et al. | |
| 6,181,973 B1 | 1/2001 | Ceron et al. | |
| 6,188,932 B1 | 2/2001 | Lindegren | |
| 6,240,322 B1 | 5/2001 | Peterfeso et al. | |
| 6,304,613 B1 * | 10/2001 | Koller .................. | G06K 19/0701 235/492 |
| 6,304,786 B1 | 10/2001 | Heil et al. | |
| 6,324,434 B2 | 11/2001 | Coe et al. | |
| 6,405,091 B1 | 6/2002 | Vachon et al. | |
| 6,482,152 B2 | 11/2002 | Kim | |
| 6,510,347 B2 | 1/2003 | Borkan | |
| 6,659,352 B1 | 12/2003 | Asada et al. | |
| 6,678,179 B2 * | 1/2004 | Buehring ................ | H02M 3/28 363/125 |
| 7,191,007 B2 | 3/2007 | Desai et al. | |
| 7,191,013 B1 | 3/2007 | Miranda et al. | |
| 7,289,028 B2 * | 10/2007 | Kofler ................ | G06K 19/0701 340/572.4 |
| 7,573,368 B2 * | 8/2009 | Conraux .................. | G01S 13/75 235/380 |
| 7,703,677 B2 * | 4/2010 | Alihodzic .......... | G06K 19/0701 235/451 |
| 7,756,223 B2 | 7/2010 | Missoni | |
| 8,120,487 B2 * | 2/2012 | Chang ...................... | G06F 1/32 340/572.1 |
| 8,280,272 B2 * | 10/2012 | Kim .................... | G03G 15/0283 399/37 |
| 8,299,652 B2 | 10/2012 | Sample et al. | |
| 8,452,421 B2 | 5/2013 | Thenuwara et al. | |
| 8,497,658 B2 * | 7/2013 | Von Novak ............. | H02J 7/025 320/108 |
| 8,538,541 B2 | 9/2013 | Milojevic et al. | |
| 8,634,928 B1 | 1/2014 | O'Driscoll et al. | |
| 8,641,644 B2 | 2/2014 | Freeman et al. | |
| 8,655,451 B2 | 2/2014 | Klosterman et al. | |
| 8,855,786 B2 | 10/2014 | Derbas et al. | |
| 8,891,270 B2 | 11/2014 | Song et al. | |
| 8,901,775 B2 | 12/2014 | Armstrong et al. | |
| 8,901,778 B2 | 12/2014 | Kesler et al. | |
| 8,901,779 B2 | 12/2014 | Kesler et al. | |
| 8,937,825 B2 * | 1/2015 | Lee ........................ | H02M 7/217 363/89 |
| 8,972,502 B2 | 3/2015 | Beslic et al. | |
| 9,276,457 B2 * | 3/2016 | Taillardat ................ | H02P 27/14 |
| 9,367,784 B2 * | 6/2016 | Tramoni ............ | G06K 19/0701 |
| 9,504,842 B2 | 11/2016 | Guardiani et al. | |
| 9,537,428 B2 * | 1/2017 | Hytten ...................... | H02J 3/36 |
| 9,592,397 B2 | 3/2017 | Hansen et al. | |
| 9,692,324 B2 * | 6/2017 | Bieler .................. | H02N 2/0075 |
| 9,821,159 B2 | 11/2017 | Ackermann et al. | |
| 9,831,681 B2 * | 11/2017 | Shimokawa ............. | H01F 38/14 |
| 9,831,719 B2 * | 11/2017 | Lee ........................ | H02J 5/005 |
| 10,004,913 B2 | 6/2018 | Poon et al. | |
| 2001/0044588 A1 | 11/2001 | Mault | |
| 2001/0051766 A1 | 12/2001 | Gazdzinski | |
| 2002/0042637 A1 | 4/2002 | Stover | |
| 2003/0055406 A1 | 3/2003 | Lebel et al. | |
| 2003/0158584 A1 | 8/2003 | Cates et al. | |
| 2004/0193229 A1 | 9/2004 | Starkebaum et al. | |
| 2005/0043765 A1 | 2/2005 | Williams et al. | |
| 2005/0151696 A1 | 7/2005 | Govari et al. | |
| 2005/0245989 A1 | 11/2005 | Davis | |
| 2005/0288596 A1 | 12/2005 | Eigler et al. | |
| 2006/0061323 A1 | 3/2006 | Cheng et al. | |
| 2006/0074450 A1 | 4/2006 | Boveja et al. | |
| 2006/0149330 A1 | 7/2006 | Mann et al. | |
| 2006/0161225 A1 | 7/2006 | Sormann et al. | |
| 2006/0210279 A1 | 9/2006 | Hillis et al. | |
| 2006/0224225 A1 | 10/2006 | Ransbury et al. | |
| 2006/0241524 A1 | 10/2006 | Lee et al. | |
| 2006/0253044 A1 | 11/2006 | Zhang et al. | |
| 2007/0032734 A1 | 2/2007 | Najafi et al. | |
| 2007/0156205 A1 | 7/2007 | Larson et al. | |
| 2007/0222542 A1 | 9/2007 | Joannopoulos et al. | |
| 2007/0282378 A1 | 12/2007 | Huang et al. | |
| 2008/0021532 A1 | 1/2008 | Kveen et al. | |
| 2008/0039904 A1 | 2/2008 | Bulkes et al. | |
| 2008/0045989 A1 | 2/2008 | Welborn | |
| 2008/0103578 A1 | 5/2008 | Gerber | |
| 2008/0132981 A1 | 6/2008 | Gerber | |
| 2008/0161803 A1 | 7/2008 | Oral et al. | |
| 2008/0197710 A1 | 8/2008 | Kreitz et al. | |
| 2008/0234598 A1 | 9/2008 | Snyder et al. | |
| 2008/0300654 A1 | 12/2008 | Lambert et al. | |
| 2008/0300660 A1 | 12/2008 | John | |
| 2009/0105782 A1 | 4/2009 | Mickle et al. | |
| 2009/0128262 A1 | 5/2009 | Lee et al. | |
| 2009/0157147 A1 | 6/2009 | Cauller et al. | |
| 2009/0171408 A1 | 7/2009 | Solem | |
| 2009/0187230 A1 | 7/2009 | Dilorenzo | |
| 2009/0204170 A1 | 8/2009 | Hastings et al. | |
| 2009/0275956 A1 | 11/2009 | Burnes et al. | |
| 2009/0281597 A1 | 11/2009 | Parramon et al. | |

(56) References Cited

U.S. PATENT DOCUMENTS

| | | |
|---|---|---|
| 2009/0292336 A1 | 11/2009 | Nishida et al. |
| 2010/0081895 A1 | 4/2010 | Zand |
| 2010/0145418 A1 | 6/2010 | Zhang et al. |
| 2010/0161002 A1 | 6/2010 | Aghassian et al. |
| 2010/0168817 A1 | 7/2010 | Yamamoto et al. |
| 2010/0264748 A1 | 10/2010 | Tucker |
| 2010/0292629 A1 | 11/2010 | Dacey et al. |
| 2011/0034886 A1 | 2/2011 | Elbe et al. |
| 2011/0093036 A1 | 4/2011 | Mashiach |
| 2011/0125078 A1 | 5/2011 | Denison et al. |
| 2011/0144510 A1 | 6/2011 | Ryu et al. |
| 2011/0184337 A1 | 7/2011 | Evans et al. |
| 2011/0190849 A1 | 8/2011 | Faltys et al. |
| 2011/0276110 A1 | 11/2011 | Whitehurst et al. |
| 2011/0301670 A1 | 12/2011 | Gross et al. |
| 2012/0004708 A1 | 1/2012 | Chen et al. |
| 2012/0123508 A1 | 5/2012 | Wentz et al. |
| 2012/0197352 A1 | 8/2012 | Carbunaru et al. |
| 2012/0203079 A1 | 8/2012 | McLaughlin |
| 2012/0203306 A1 | 8/2012 | Sarvazyan |
| 2012/0235500 A1 | 9/2012 | Ganem et al. |
| 2012/0235634 A1 | 9/2012 | Hall et al. |
| 2012/0245444 A1 | 9/2012 | Otis et al. |
| 2012/0253261 A1 | 10/2012 | Poletto et al. |
| 2012/0283800 A1 | 11/2012 | Perryman et al. |
| 2012/0296329 A1 | 11/2012 | Ng |
| 2012/0330384 A1 | 12/2012 | Perryman et al. |
| 2013/0012866 A1 | 1/2013 | Deem et al. |
| 2013/0023943 A1 | 1/2013 | Parramon et al. |
| 2013/0053767 A1 | 2/2013 | Pivonka et al. |
| 2013/0079861 A1 | 3/2013 | Reinert et al. |
| 2013/0141794 A1 | 6/2013 | Najiminaini et al. |
| 2013/0211469 A1 | 8/2013 | Lamont et al. |
| 2013/0215979 A1 | 8/2013 | Yakovlev et al. |
| 2013/0261703 A1 | 10/2013 | Chow et al. |
| 2013/0310901 A1 | 11/2013 | Perryman et al. |
| 2013/0336095 A1 | 12/2013 | Seppa et al. |
| 2014/0142507 A1 | 5/2014 | Armes |
| 2014/0203823 A1 | 7/2014 | Joshi |
| 2014/0275847 A1 | 9/2014 | Perryman et al. |
| 2014/0288393 A1 | 9/2014 | Grevious et al. |
| 2014/0324138 A1 | 10/2014 | Wentz et al. |
| 2015/0335285 A1 | 11/2015 | Poon et al. |
| 2016/0113671 A1 | 4/2016 | Berger |
| 2016/0228183 A1 | 8/2016 | Urzhumov |
| 2016/0228720 A1 | 8/2016 | Urzhumov |
| 2017/0065828 A1 | 3/2017 | Poon et al. |
| 2017/0095667 A1 | 4/2017 | Yakovlev et al. |

FOREIGN PATENT DOCUMENTS

| | | |
|---|---|---|
| WO | WO2013/035092 A2 | 3/2013 |
| WO | WO2014/006510 A2 | 1/2014 |
| WO | WO2014/153219 A1 | 9/2014 |
| WO | WO2014/153228 A1 | 9/2014 |
| WO | WO2015/039108 A2 | 3/2015 |
| WO | WO2015/196164 A2 | 12/2015 |
| WO | WO2016/127130 A1 | 8/2016 |

OTHER PUBLICATIONS

Poher et al.; Micro-LED arrays: a tool for two-dimensional neuron stimulation; Journal of Physics D: Applied Physics; 41(9); 094014; 10 pages; Apr. 4, 2008.

Wentz et al.; A wireless powered and controlled device for optical neural control of freely-behaving animals; Journal of Neural Engineering; 8(4); 046021. dol: 10.1088/1741-2560/8/4/046021; 18 pages; Aug. 2011.

Ball; Wireless power for tiny medical devices; Physics; 6; 57; 3 pages; May 17, 2013.

Ho et al.; Midfield wireless powering for implantable systems; Proc. IEEE; vol. 101; No. 6; Apr. 4, 2013; 10 pages; retrieved Apr. 21, 2014 from the internet: http://web.stanford.edu/group/poongroup/cgi-bin/wordpress/wp-content/uploads/2013/05/PIEEE%202013%20Ho.pdf.

Kim et al.; Midfield wireless powering of subwavelength autonomous devices; Phys. Rev. Lett.; 110(20); 203905; May 17, 2013.

Kim et al.; Wireless power transfer to a cardiac implant; Appl. Phys. Lett.; 101; 073701; 2012; 5 pages; Aug. 13, 2012.

Kim et al.; Wireless power transfer to miniature implants: transmitter optimization; IEEE Trans. Antennas and Propagation; vol. 60; No. 10; pp. 4838-4845; Oct. 2012.

Park et al.; Enhancement of wireless power transmission into biological tissues using a high surface impedance ground plane; Progress in Electromagnetics Research; 135; pp. 123-136; 2013; retrieved Apr. 29, 2015 from the internet: http://onlinewww.jpier.org/PIER/pier135/08.12110902.pdf.

Thomas et al.; Modulated backscatter for ultra-low power uplinks from wearable and implantable devices; In Proceedings of the 2012 ACM workshop on Medical communication systems; 6 pages; retrieved from the internet (http://conferences.sigcomm.org/sigcomm/2012/paper/medcomm/p1.pdf); Aug. 13, 2012.

Xu et al.; A novel mat-based system for position-varying wireless power transfer to biomedical implants; IEEE Transactions on Magnetics; 49(8); pp. 4774-4779; Aug. 2013.

Yeh et al.; Wirelessly powering miniature implants for optogenetic stimulation; Appl. Phy. Lett.; 103; 163701; 4 pages; Oct. 8, 2013.

Zhao et al.; RF evanescent-mode cavity resonator for passive wireless sensor applications; Sensors and Actuators A; 161(1-2); pp. 322-328; Jun. 1, 2010.

Poon et al.; U.S. Appl. No. 16/505,425 entitled "Wireless implantable sensing devices," filed Jul. 8, 2019.

* cited by examiner

METHODS AND APPARATUS FOR POWER CONVERSION AND DATA TRANSMISSION IN IMPLANTABLE SENSORS, STIMULATORS, AND ACTUATORS

CROSS REFERENCE TO RELATED APPLICATIONS

This application is a continuation of U.S. application Ser. No. 14/637,148, filed Mar. 3, 2015, now U.S. patent Ser. No. 10/004,913, which application claims the benefit of U.S. Provisional Application No. 61/947,240, filed Mar. 3, 2014, titled "METHODS FOR POWER CONVERSION AND DATA TRANSMISSION IN IMPLANTABLE SENSORS, STIMULATORS, AND ACTUATORS", both of which are fully incorporated herein by reference.

INCORPORATION BY REFERENCE

All publications and patent applications mentioned in this specification are herein incorporated by reference to the same extent as if each individual publication or patent application was specifically and individually indicated to be incorporated by reference.

FIELD

This disclosure is related generally to wireless power transfer. More specifically, this disclosure relates to delivering wireless power through tissue into a device implanted in a human or animal.

BACKGROUND

Current implanted electrostimulation systems typically include a large impulse generator including a titanium case enclosing the power source and circuitry used to generate the electrical pulses. Due to the large size of these devices, the device itself is typically implanted within a cavity in the body such as under the clavicle, below the rib cage, in the lower abdominal region, or in the upper buttock. Electrical pulses are then delivered to a targeted nerve or muscle region via leads routed underneath the skin. Problems associated with this current approach include pocket infections, lead dislodgment, lead fracture or perforation, muscle tear due to implanting in or pulling out the leads, and limited locations for the placement of the electrodes.

The vast majority of wirelessly powered implantable devices operate in the strongly coupled regime, e.g., inductive coupling. In conventional wireless approaches using inductive coupling, the evanescent components outside tissue (near the source) remain evanescent inside tissue which does not allow for effective depth penetration of the wireless energy. Rectification techniques utilized for inductive coupling devices results in highly inefficient power conversion. For example, the rectification efficiency can be as low as 5% using these techniques.

Many conventional implantable devices use a backscattered (BS) technique for data transmission due to its simplicity in implementation. However, this technique can be very sensitive to the heterogeneous nature of the tissue medium and the data rate is limited. Furthermore, the data transmission performance can decay when implantable devices are placed deep in the tissue. To solve this problem, an active transmitter may be implemented but may consume substantial amount of power due to complexity in implementation.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

SUMMARY OF THE DISCLOSURE

Figure 1:
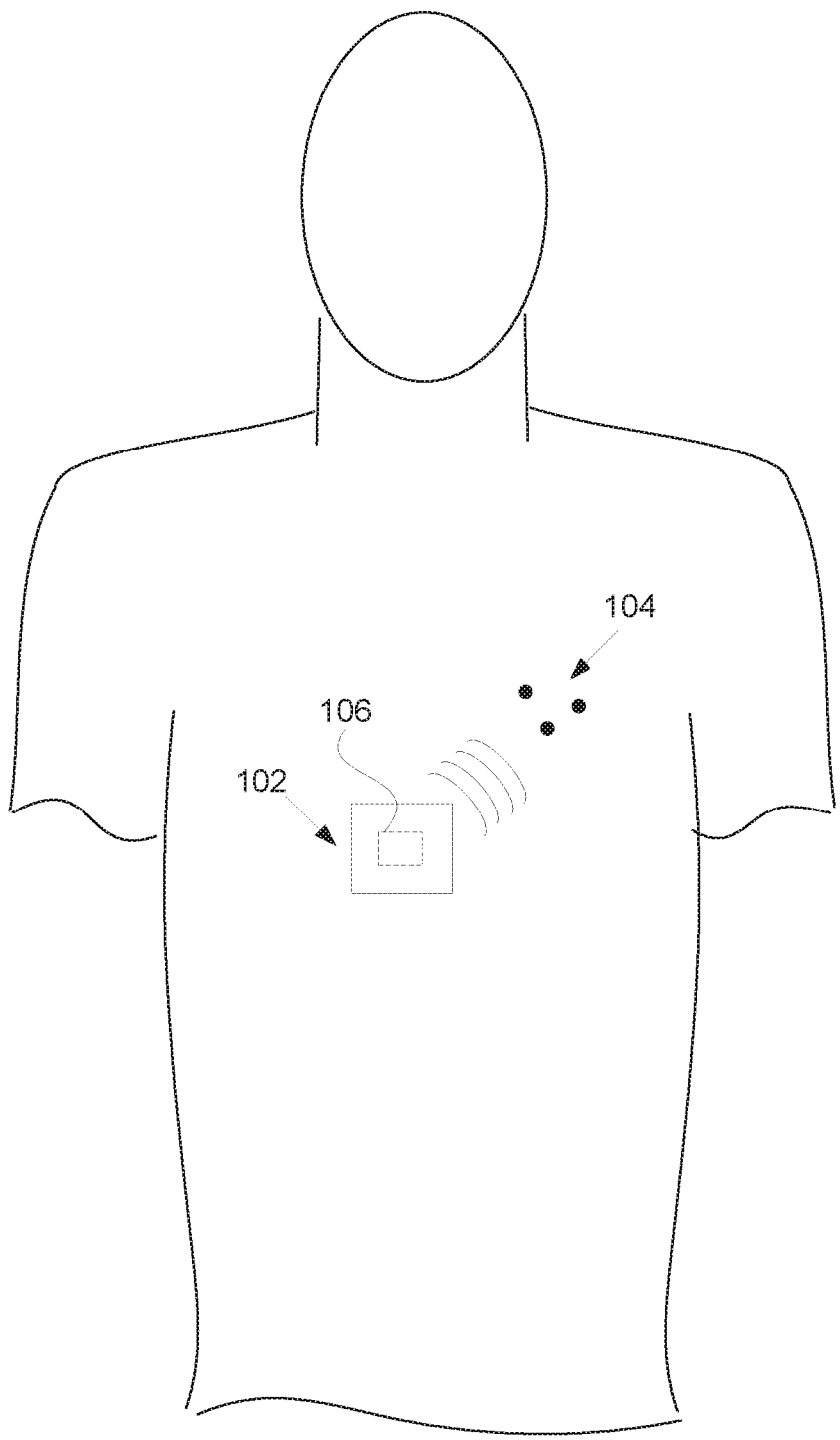
FIG. 1 is a schematic diagram showing an external wireless power transmitting module and one or more implanted modules configured to receive wireless power.

A wireless power receiving device is provided, comprising a coupler configured to induce an alternating current or voltage in the presence of electromagnetic fields or oscillating sound pressure waves, a first AC-DC conversion chain configured to rectify the induced alternating current or voltage into a first DC current or voltage in a first energy domain, a first DC load coupled to the first AC-DC conversion chain, a second AC-DC conversion chain arranged in parallel with the first AC-DC conversion chain and configured to rectify the induced alternating current or voltage into a second DC current or voltage in a second energy domain, and a second DC load coupled to the second AC-DC conversion chain.

In some embodiments, the first or second AC-DC conversion chains comprise a rectifier stage.

In one embodiment, the first or second AC-DC conversion chains comprise two or more rectifier stages.

In another embodiment, the first or second AC-DC conversion chains comprise a rectifier stage in series with a DC-DC conversion circuit.

In one embodiment, the first or second AC-DC conversion chains comprise two or more rectifier stages in series with a DC-DC conversion circuit.

In another embodiment, the first or second AC-DC conversion chains comprise a rectifier stage in parallel with a capacitor and a DC-DC conversion circuit, with a battery connected to an output of the DC-DC conversion circuit.

In an additional embodiment, the first or second AC-DC conversion chains comprise two or more rectifier stages in parallel with a capacitor and a DC-DC conversion circuit, with a battery connected to an output of the DC-DC conversion circuit.

In some embodiments, the first or second AC-DC conversion chains comprise a rectifier stage in series with a DC-DC conversion circuit and a battery.

In one embodiment, the first or second AC-DC conversion chains comprise two or more rectifier stages in series with a DC-DC conversion circuit and a battery.

In some embodiments, the first or second AC-DC conversion chains comprise a rectifier stage in series with a DC-DC conversion circuit, a battery, and a second DC-DC conversion circuit.

In other embodiments, the first or second AC-DC conversion chains comprise two or more rectifier stages in series with a DC-DC conversion circuit, a battery, and a second DC-DC conversion circuit.

In one embodiment, the first DC current or voltage in the first energy domain is optimized for the first DC load.

In some embodiments, the second DC current or voltage in the first energy domain is optimized for the second DC load.

In other embodiments, the first energy domain comprises a low-voltage domain.

In an extra embodiment, the first DC load comprises sensor circuitry, digital logic, a data transceiver, an analog oscillator, or an analog clock.

In some embodiments, the second energy domain comprises a high-voltage domain.

In other embodiments, the second DC load comprises a battery, a stimulator, or an actuator.

A wireless power system is also provided, comprising an external power transmitting module configured to manipulate evanescent fields to control propagating fields inside tissue generating a spatially focusing and adaptive steering field inside tissue, and an implantable module configured to receive wireless power from the external power transmitting module via the spatially focusing and adaptive steering field, the implantable module including a coupler configured to induce an alternating current or voltage in the presence of electromagnetic fields or oscillating sound pressure waves, a first AC-DC conversion chain configured to rectify the induced alternating current or voltage into a first DC current or voltage in a first energy domain, a first DC load coupled to the first AC-DC conversion chain, a second AC-DC conversion chain arranged in parallel with the first AC-DC conversion chain and configured to rectify the induced alternating current or voltage into a second DC current or voltage in a second energy domain, and a second DC load coupled to the second AC-DC conversion chain.

A wireless power receiving device is further provided, comprising a coupler configured to induce an alternating current or voltage in the presence of electromagnetic fields or oscillating sound pressure waves, an AC-DC conversion chain comprising a rectifier stage in series with a DC-DC conversion circuit, the AC-DC conversion chain being configured to rectify the induced alternating current or voltage into a DC current or voltage, and a DC load coupled to the AC-DC conversion chain.

A wireless power receiving device is also provided, comprising a coupler configured to induce an alternating current or voltage in the presence of electromagnetic fields or oscillating sound pressure waves, an AC-DC conversion chain comprising two or more rectifier stages in series with a DC-DC conversion circuit, with a battery connected to an output of the DC-DC conversion circuit, the AC-DC conversion chain being configured to rectify the induced alternating current or voltage into a DC current or voltage, and a DC load coupled to the AC-DC conversion chain.

A wireless power receiving device is provided, comprising a coupler configured to induce an alternating current or voltage in the presence of electromagnetic fields or oscillating sound pressure waves, an AC-DC conversion chain comprising a rectifier stage in parallel with a capacitor and a DC-DC conversion circuit, with a battery connected to an output of the DC-DC conversion circuit, the AC-DC conversion chain being configured to rectify the induced alternating current or voltage into a DC current or voltage, and a DC load coupled to the AC-DC conversion chain.

A wireless power receiving device is further provided, comprising a coupler configured to induce an alternating current or voltage in the presence of electromagnetic fields or oscillating sound pressure waves, an AC-DC conversion chain comprising two or more rectifier stages in parallel with a capacitor and a DC-DC conversion circuit, with a battery connected to an output of the DC-DC conversion circuit, the AC-DC conversion chain being configured to rectify the induced alternating current or voltage into a DC current or voltage, and a DC load coupled to the AC-DC conversion chain.

A wireless power receiving device is also provided, comprising a coupler configured to induce an alternating current or voltage in the presence of electromagnetic fields or oscillating sound pressure waves, an AC-DC conversion chain comprising a rectifier stage in series with a DC-DC conversion circuit and a battery, the AC-DC conversion chain being configured to rectify the induced alternating current or voltage into a DC current or voltage, and a DC load coupled to the AC-DC conversion chain.

A wireless power receiving device is further provided, comprising a coupler configured to induce an alternating current or voltage in the presence of electromagnetic fields or oscillating sound pressure waves, an AC-DC conversion chain comprising two or more rectifier stages in series with a DC-DC conversion circuit and a battery, the AC-DC conversion chain being configured to rectify the induced alternating current or voltage into a DC current or voltage, and a DC load coupled to the AC-DC conversion chain.

A wireless power receiving device is provided, comprising a coupler configured to induce an alternating current or voltage in the presence of electromagnetic fields or oscillating sound pressure waves, an AC-DC conversion chain comprising a rectifier stage in series with a DC-DC conversion circuit, a battery, and a second DC-DC conversion circuit, the AC-DC conversion chain being configured to rectify the induced alternating current or voltage into a DC current or voltage, and a DC load coupled to the AC-DC conversion chain.

DETAILED DESCRIPTION

Implantable devices/sensors can be wirelessly powered by controlling propagating electromagnetic waves in tissue. The implantable devices can be implanted in humans or in other animals such as pets, livestock, or laboratory animals such as mice, rats, and other rodents. Such implantable devices/sensors can be implanted at target locations in a patient, as non-limiting examples, to stimulate areas such as the heart, and/or to sense biological, physiological, chemical attributes of the blood, tissue, and other patient aspects.

Difficulties in achieving wireless power transfer can occur in the mismatch between the size of the implantable devices/sensors and the power transfer source, the depth of the devices/sensors in a patient, and additionally the spatial arrangement (for example, displacement and orientation) of the devices/sensors relative to the power transfer source.

Certain embodiments of the present disclosure are directed to manipulation of evanescent fields outside a patient's tissue with sub-wavelength structures to excite/control propagating fields inside a patient's tissue and thereby generate a spatially focusing and adaptive steering field/signal in the tissue. A sub-wavelength structure generates fields that are evanescent in nature near the source.

This disclosure provides embodiments of sub-wavelength structures and methods for controlling the excitation of those structures to excite the propagating modes inside tissue from the evanescent modes outside tissue. As a result, this approach is very effective in transporting energy to absorption-limited depth inside tissue. The designs disclosed herein include structures that use tissue as a dielectric waveguide to tunnel energy into the body. The energy can be received by an implanted module which will be discussed below, to allow for wireless power transfer to tiny implanted devices (millimeter or smaller in scale) at depths unattainable with conventional inductive coupling technology.

This disclosure provides a midfield wireless powering approach that integrates an external module configured to transmit wireless power, and one or more implanted modules configured to receive wireless power that combines an impulse generator and at least one stimulation electrode together into a small, leadless, implantable device. In some embodiments, the implanted module can be small enough to be delivered via a catheter or a hypodermic needle. For example, the implanted module can be as small as a few millimeters in diameter (2-3 mm) down to having diameters on the order of 100's of microns or less. The external and implant modules allow for the transfer of wireless power to nearly any location in the body at performance levels far exceeding requirements for both complex electronics and physiological stimulation. Because the implanted modules are small, they can be injected into the targeted nerve or muscle region directly without the need for leads and extensions, to provide sensing and stimulation to the targeted nerve, muscle, or tissue region. When the implantable devices are wirelessly powered by electromagnetic fields, power can be focused within human tissue in the electromagnetic midfield using frequencies between approximately 400 MHz and 2.5 GHz. This allows for much smaller devices that can be injected deep in the tissue using a catheter or a needle. Further details on the implanted and external modules described herein can be found in International Application No. PCT/US2014/055885, filed Sep. 16, 2014, incorporated herein by reference.

This disclosure provides methods to increase the efficiency of rectification and power management of wirelessly powered implantable devices that are operated in a weakly coupled regime using midfield wireless powering approach. With this approach, the transmission of electromagnetic fields or oscillating sound pressure waves from the external module to the implantable device(s) is very low, ranging from tens to hundreds of millivolts. Rectification techniques present in this disclosure, can be as high as 50%.

This disclosure further provides methods and apparatus for data transmission to and from the implantable device(s) to the external module that works in a heterogeneous tissue medium, consumes minimal power, and supports a high data rate.

FIG. 1 is a schematic figure showing an external wireless power transmitting module 102 external to a patient and one or more implantable modules 104 disposed within the patient. The external wireless power transmitting module can include one or more sub-wavelength structures 106 configured to manipulate evanescent fields outside a patient's tissue to excite/control propagating fields inside a patient's tissue to generate a spatially focusing and adaptive steering field/signal in the tissue. The one or more implanted modules are configured to receive wireless power from the external module. The implanted modules can optionally include features for sensing and/or stimulating tissue, such as an electrode. Because the power levels supported by a midfield wireless powering approach far exceed requirements for microelectronic technologies, more sophisticated functions can be implemented such as real-time monitoring of chronic disease states or closed-loop biological sensing and control by the implanted module.

Figure 2:
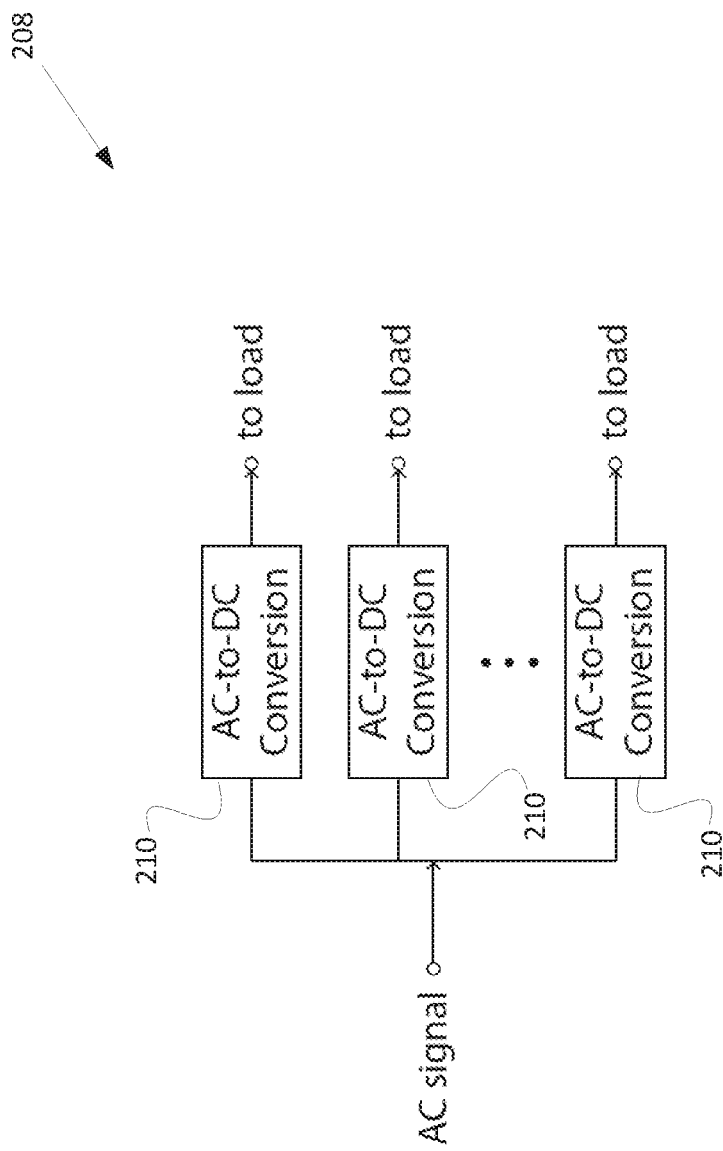
FIG. 2 shows embodiments of a power conversion module that can be included in an implanted device that receives wireless power.

FIG. 2 shows an embodiment of a power conversion module 208 that can be included in the implantable module of FIG. 1. The power conversion module 208 can include one or more AC-to-DC conversion chains 210 arranged in parallel. Each chain 210 can be configured to rectify the alternating current/voltage (AC) induced by the electromagnetic fields or oscillating sound pressure waves and received by the implanted modules into direct current/voltage (DC), supplying energy to one or more loads on the implanted device. Since the implanted modules described herein can be fully customized with many different loads, the chains can rectify energy to loads comprising any sensor, stimulator, actuator, data transmitter, data receiver, digital controller, or any other module in or on the implantable device that must be powered by the wireless power signal. The parallel configuration of AC-to-DC conversion chains 210 in FIG. 2 can isolate noise from different loads and improve the overall conversion efficiency across voltage and energy domains (e.g., low and high voltage/energy domains).

Figure 3A:
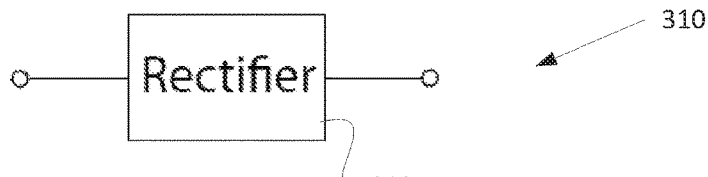
FIGS. 3A-3D illustrate various embodiments for implementing an AC-DC conversion chain in the power conversion module of FIG. 2.
Figure 3B:
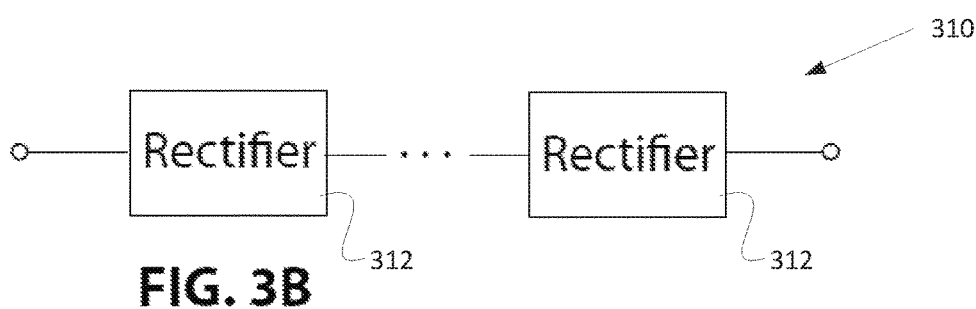

FIGS. 3A-3D illustrate various embodiments for implementing each of the AC-DC conversion chains of FIG. 2. FIG. 3A shows an AC-DC conversion chain 310 comprising a single rectifier stage 312. The output voltage using this implementation can be low, ranging from tens to hundreds of millivolts. FIG. 3B shows an AC-DC conversion chain 310 comprising two or more rectifier stages 312 placed in series to increase the output voltage. With multiple rectifiers in series, power is dissipated to the rectifier. Hence, using more than one rectifier stage to attain a high output voltage can incur significant energy loss to the rectification chain, resulting in low conversion efficiency.

Figure 3C:
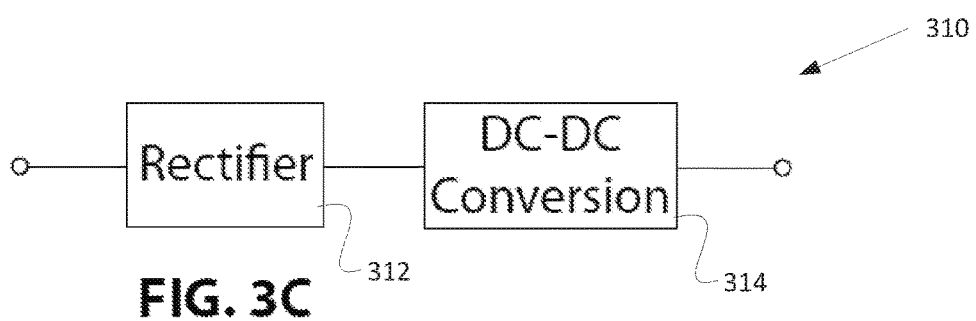
Figure 3D:
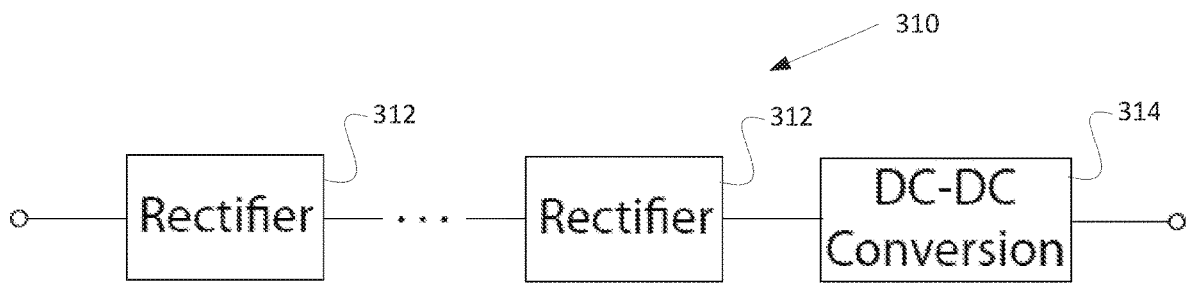

One way for increasing the efficiency of a power rectification circuit is to use DC-DC converters in conjunction with one or more rectifier stages. Thus, FIG. 3C illustrates an AC-DC conversion chain 310 comprising a single rectifier stage 312 in series with a DC-DC converter 314, and FIG. 3D shows an AC-DC conversion chain 310 comprising two or more rectifier stages 312 in series with a DC-DC converter 314. In FIGS. 3C-3D, one or more rectifier stages 312 can be used to rectify the AC voltage received by the implanted module to a low DC voltage that drives the DC-DC conversion circuits. The DC-DC conversion circuits can then convert the low DC voltage to a high DC voltage to provide power to the connected load. In some embodiments, the DC-DC conversion circuits may operate at a frequency lower than the power transmission frequency, and may operate at an efficiency that is much higher than the rectification circuit. Since the controlling circuitry for the DC-DC conversion circuits is powered by the rectified DC voltage, the DC-DC conversion circuits are isolated from the AC voltage. In this scenario, the overall conversion efficiency for an output voltage of 4 V may be as high as 50%, whereas rectification to the same voltage in embodiments FIGS. 3A and 3B may be as low as 25% in the same scenario with the same received AC power.

Figure 4A:
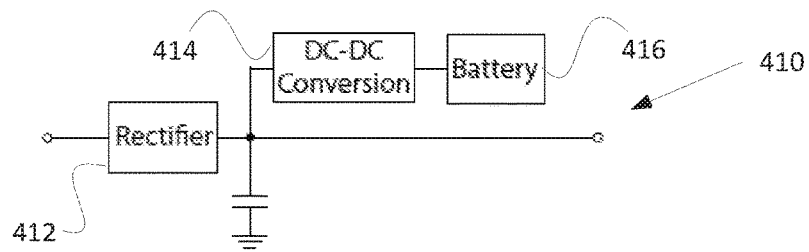
FIGS. 4A-4C show an architecture of the regulator and compares with a conventional approach.
Figure 4B:
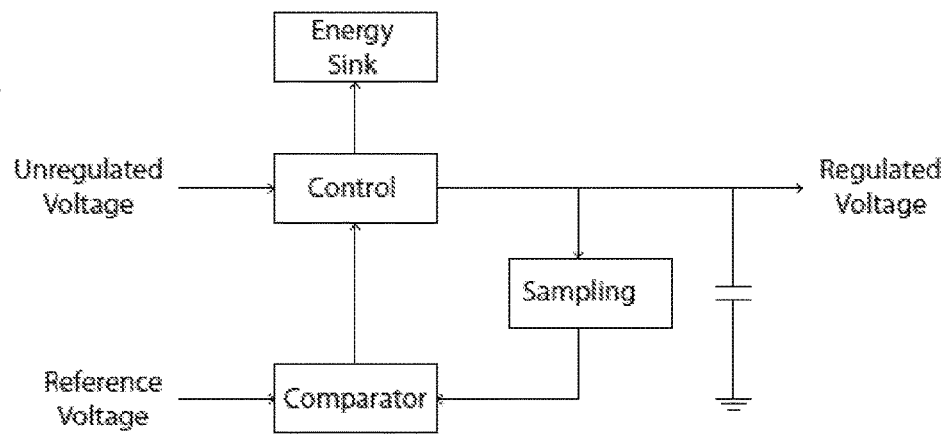
Figure 4C:
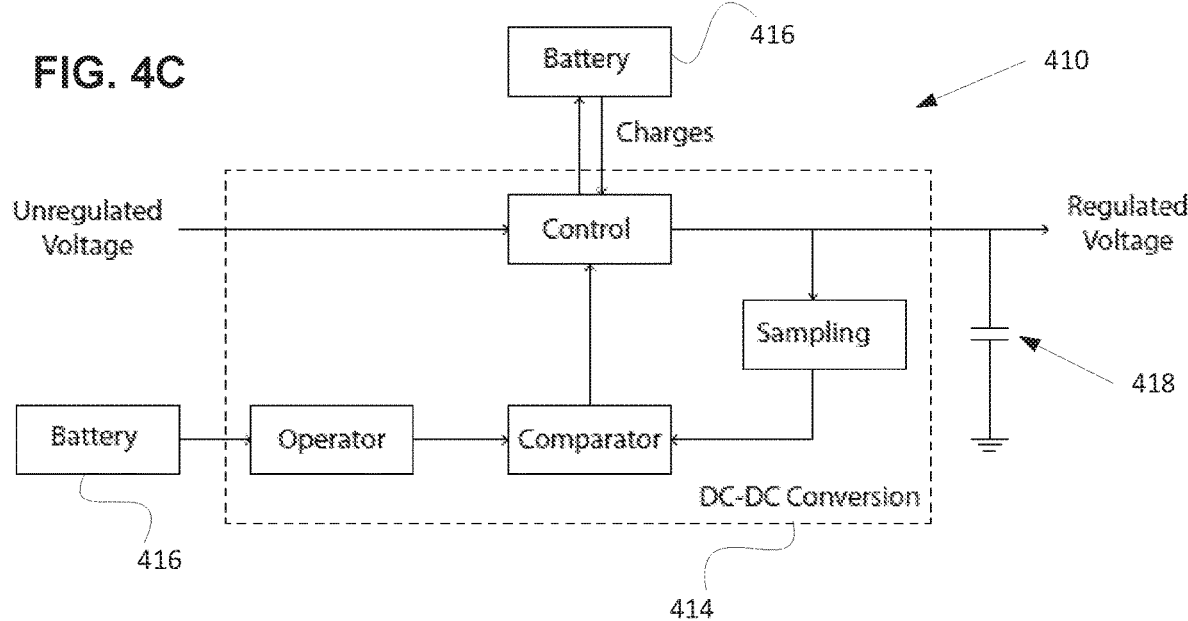

FIGS. 4A and 4C show architectures of a regulator and are compared with a conventional approach as seen in FIG. 4B. FIGS. 4A and 4C show an AC-DC conversion chain 410 including a battery 416 to maintain a stable output voltage. FIG. 4B, in contrast, shows a feedback loop for regulators where an internally generated voltage from a circuit such as a bandgap reference is used to regulate the voltage to the reference value. Power above this reference value is drained to the energy sink and is dissipated.

FIG. 4A is a high level schematic drawing of the circuit shown in FIG. 4C. In the embodiment of FIG. 4C, a battery 416 can be used as both a voltage reference and power leveler. Many sensor circuits require a level voltage in order to maintain calibration and reduce sensor noise. Battery chemistries allow the battery to maintain a stable voltage since they are non-linear with stored charge, and the voltage is dependent on electro-chemical properties of the battery cell. When the battery is connected to the output of DC-DC converter 414, it stabilizes the input voltage of the DC-DC converter in conjunction with a capacitor 418. The battery acts as an energy source for negative fluctuations in voltage, an energy storage device for positive fluctuations in voltage, and a voltage reference for deriving the operating point of the input node. Hence, the circuits of FIGS. 4A and 4C operate like a voltage regulator.

Figure 5:
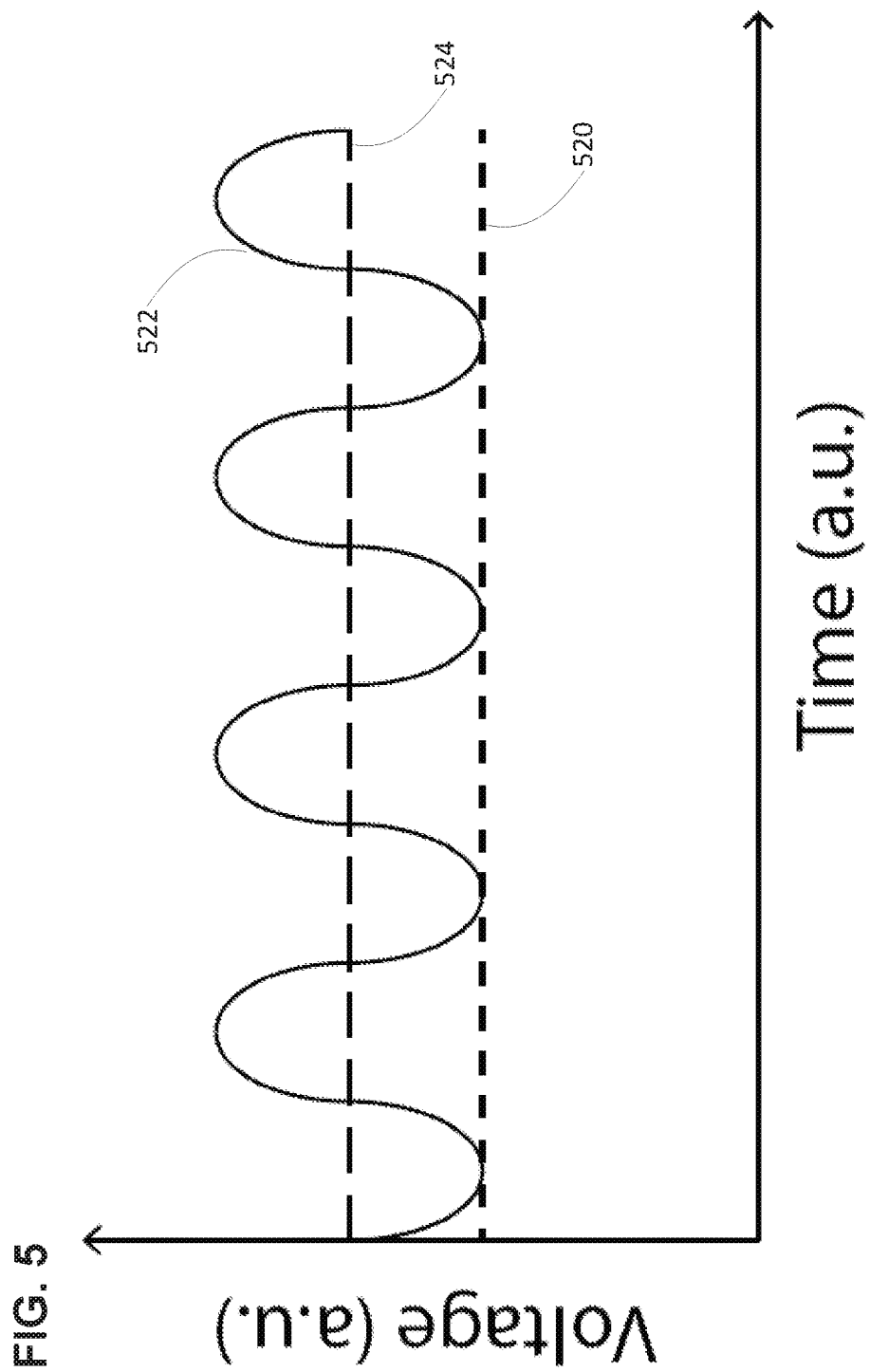
FIG. 5 compares the regulated voltage from this invention with that from conventional approaches.

FIG. 5 compares the regulated voltage from the embodiment of FIGS. 4A and 4C with that from conventional approaches. The regulated voltage 520 using the conventional approaches is the lowest bound of the unregulated voltage 522. In the disclosed embodiment, the regulated voltage 524 according to this disclosure yields the average of the unregulated voltage. So the disclosed embodiment is more efficient than conventional approaches.

Figure 6A:
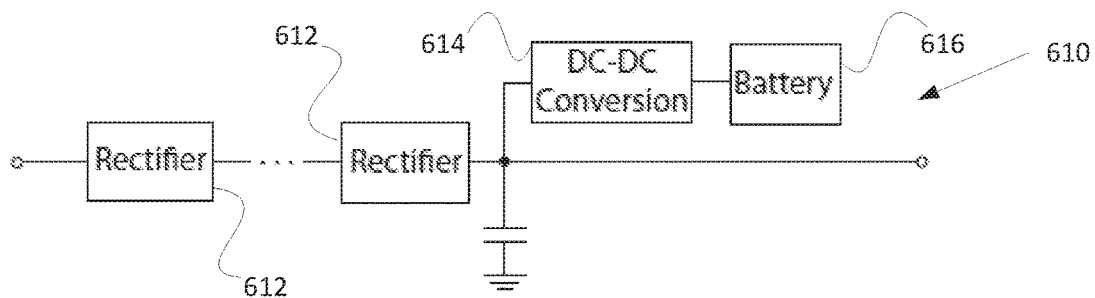
FIG. 6A-6E illustrate various embodiments for implementing an AC-DC conversion with regulator.
Figure 6B:
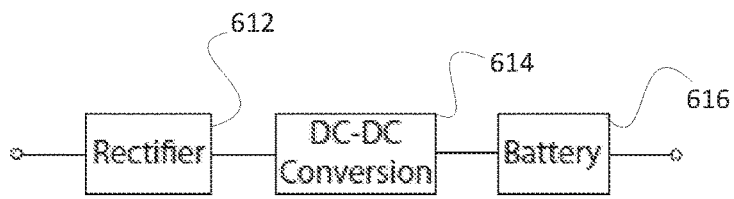
Figure 6C:
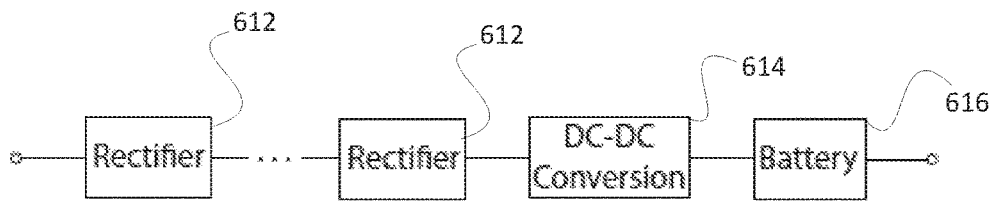
Figure 6D:
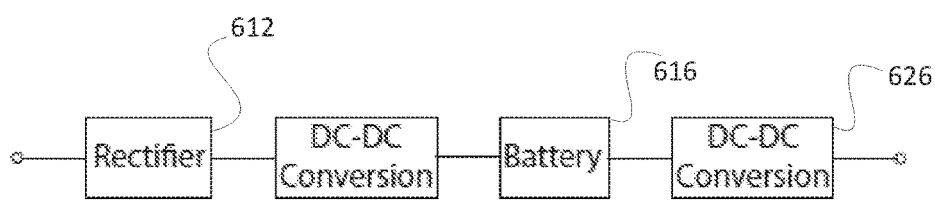
Figure 6E:
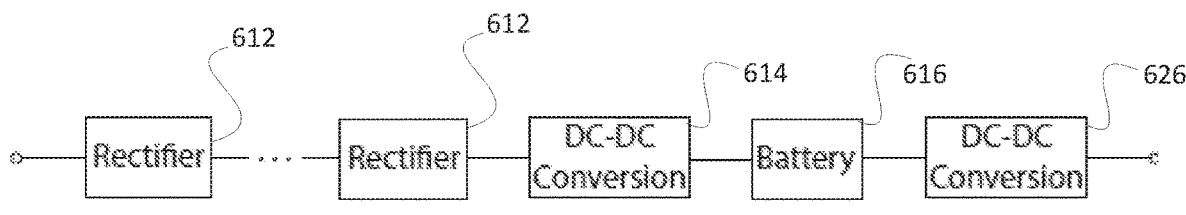

FIGS. 6A-6E show a variation of the embodiment of FIGS. 4A and 4C. In FIG. 6A, the single stage rectifier of an AC-DC conversion chain 610 is replaced by two or more rectifier stages 612, which can be connected to the DC-DC converter 614 and battery 616 as shown. In FIGS. 6B and 6C, output of the battery 616 can be used to power the loads. The embodiment of FIG. 6B includes a single rectifier stage 612, and the embodiment of FIG. 6C includes more than one rectifier stage 612 along with the DC-DC converter 614 and battery 616. For some loads, the required voltage can be lower than the output voltage of the battery, for example loads with sensor or digital logic circuits. In these cases, an additional DC-DC converter 626 is used to convert the high DC voltage from the battery 616 to a low DC voltage for the load, as shown in FIGS. 6D and 6E.

Figure 7:
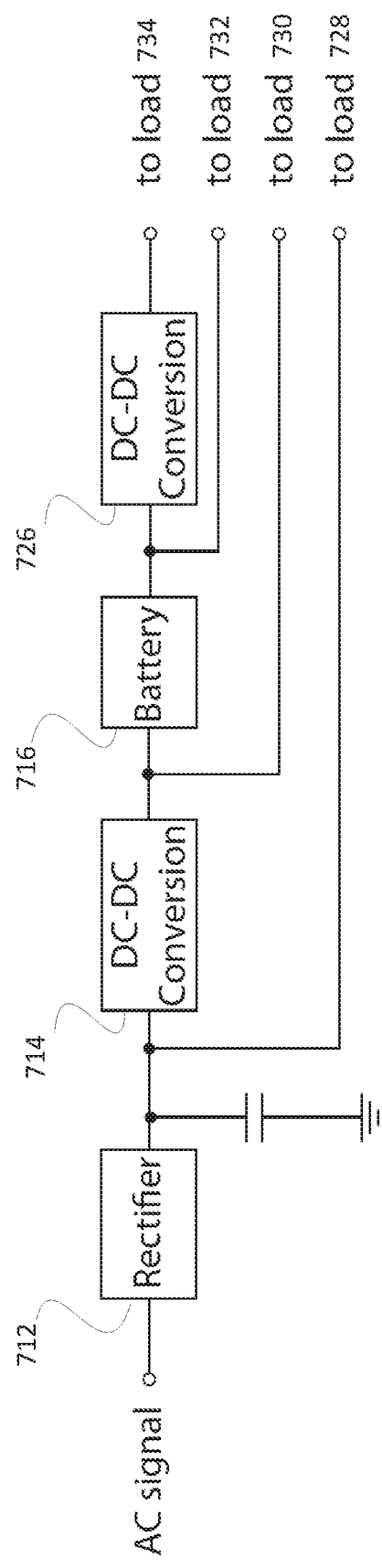
FIG. 7 shows one embodiment where various AC-DC conversion chains are combined into a single chain powering multiple loads.

The AC-DC conversion chains shown in FIGS. 3A-3D and 6A-6E can also be combined into a single chain powering up multiple loads as shown in FIG. 7. This can potentially save some components in the implementation. For example, in FIG. 7, a first load 728 can be connected to a single rectifier stage 712 (e.g., the conversion chain of FIG. 3A), a second load 730 can be connected to a single rectifier stage 712 in series with a DC-DC conversion circuit 714 (e.g., the conversion chain of FIG. 3C), a third load 732 can be connected to a single rectifier stage 712 in series with a DC-DC conversion circuit 714 and a battery 716 (e.g., the conversion chain of FIG. 6B), and a fourth load 734 can be connected to a rectifier stage 712 in series with a DC-DC conversion circuit 714, a battery 716, and a second DC-DC conversion circuit 726 (e.g., the conversion chain of FIG. 6D). It can be understood that other combinations of the conversion chains of FIGS. 3A-3D and 6A-6E can be implemented to power a plurality of loads connected to the implanted module.

Each parallel chain in FIG. 2 can be configured to yield a different output voltage that is optimized for a particular load on the implanted module. This parallel architecture can divide the circuit into low-voltage and high-voltage domains. For example, the low-voltage domain can be used to power digital circuitries in the sub-threshold region to minimize power consumption. The high-voltage domain can be used to charge up a battery of the implanted module and to power stimulation and/or actuation circuitries, which in general require high operating voltage.

Figure 8:
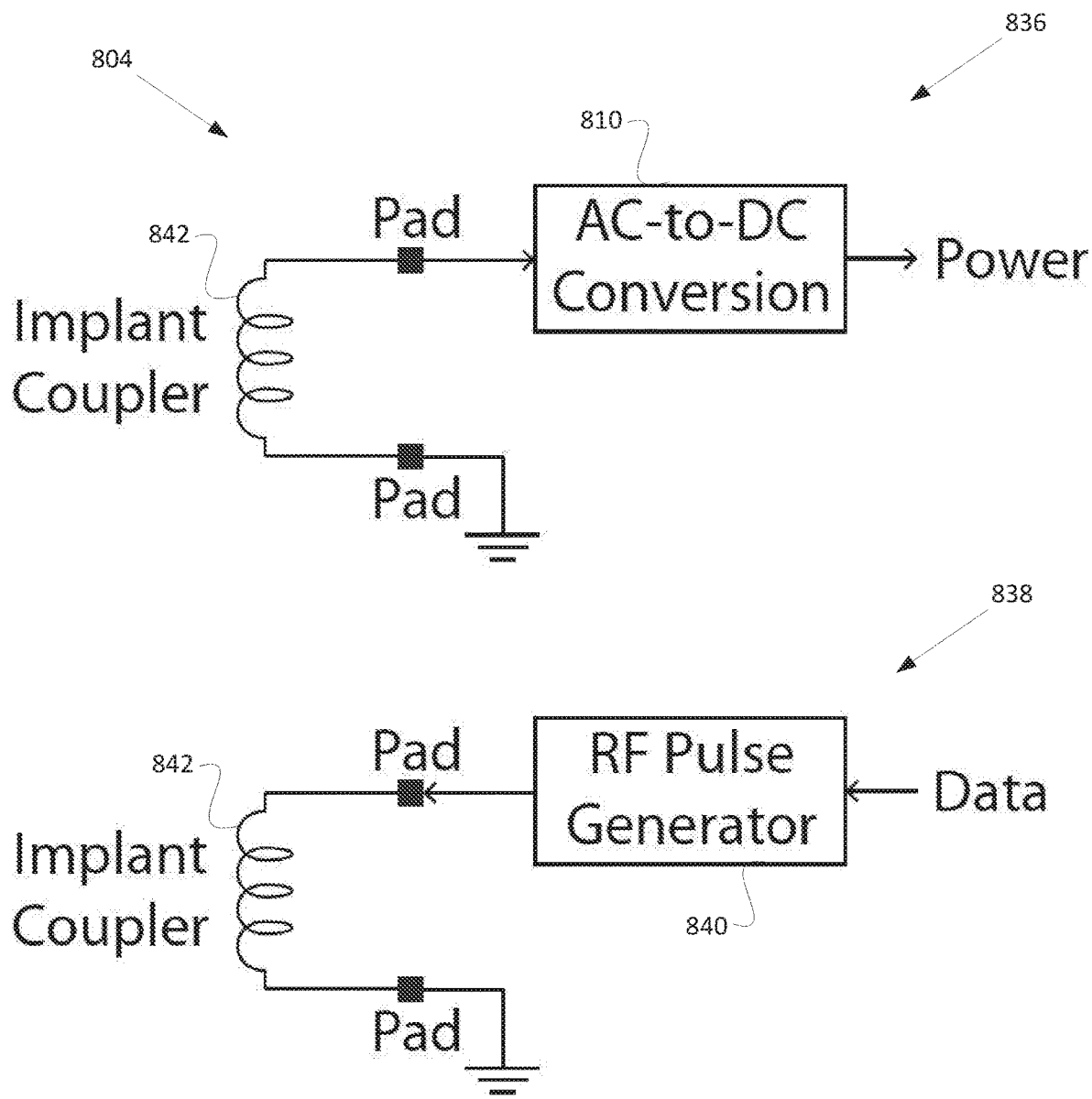
FIG. 8 shows an architecture for an implantable device including a data transmitter and a power receiver.

Another aspect of this disclosure is a data transmitter of a wirelessly powered implanted module (such as the implanted module 104 from FIG. 1). FIG. 8 illustrates an architecture for an implantable module or device 804, containing a power receiver 836, e.g., AC-DC conversion chain 810, and a data transmitter 838, including pulse generator 840. Energy for the functioning of the data transmitter can come from the power receiver, by harvesting power from the incident electromagnetic fields with the implant coupler 842.

Figure 9:
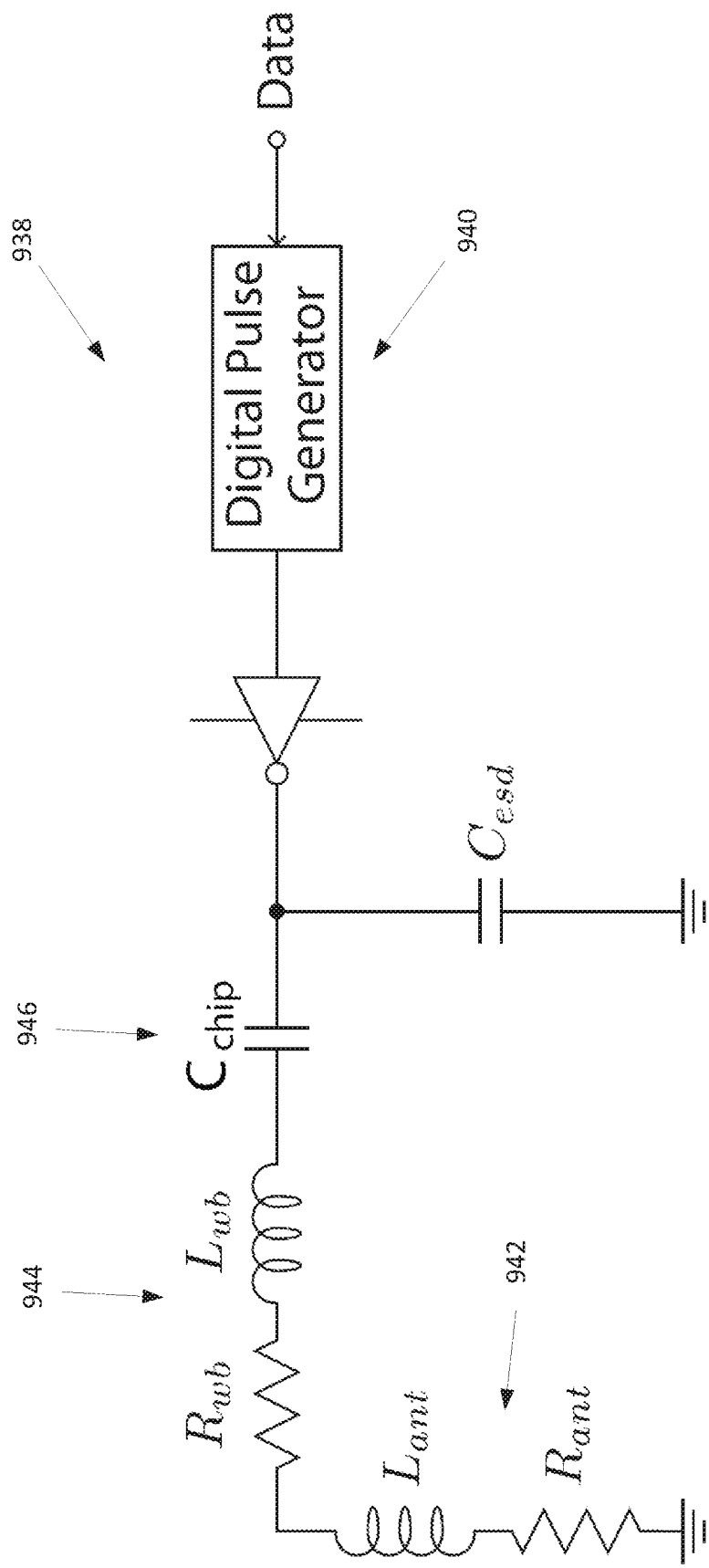
FIG. 9 is an equivalent circuit for the data transmitter architecture of FIG. 8.

FIG. 9 illustrates the equivalent circuit model of a data transmitter 938 similar to the embodiment shown in FIG. 8, including pulse generator 940. Leveraging on the inductive property of the implant coupler 942 (Lant, Rant) and wirebonds 944 from the coupler to the on-chip pads (Lwb, Rwb), they form a bandpass filter when in conjunction with an on-chip capacitor 946 (Cchip). That is, the implant coupler, wirebonds, and on-chip pads are part of the transmitter chain.

Figure 10:
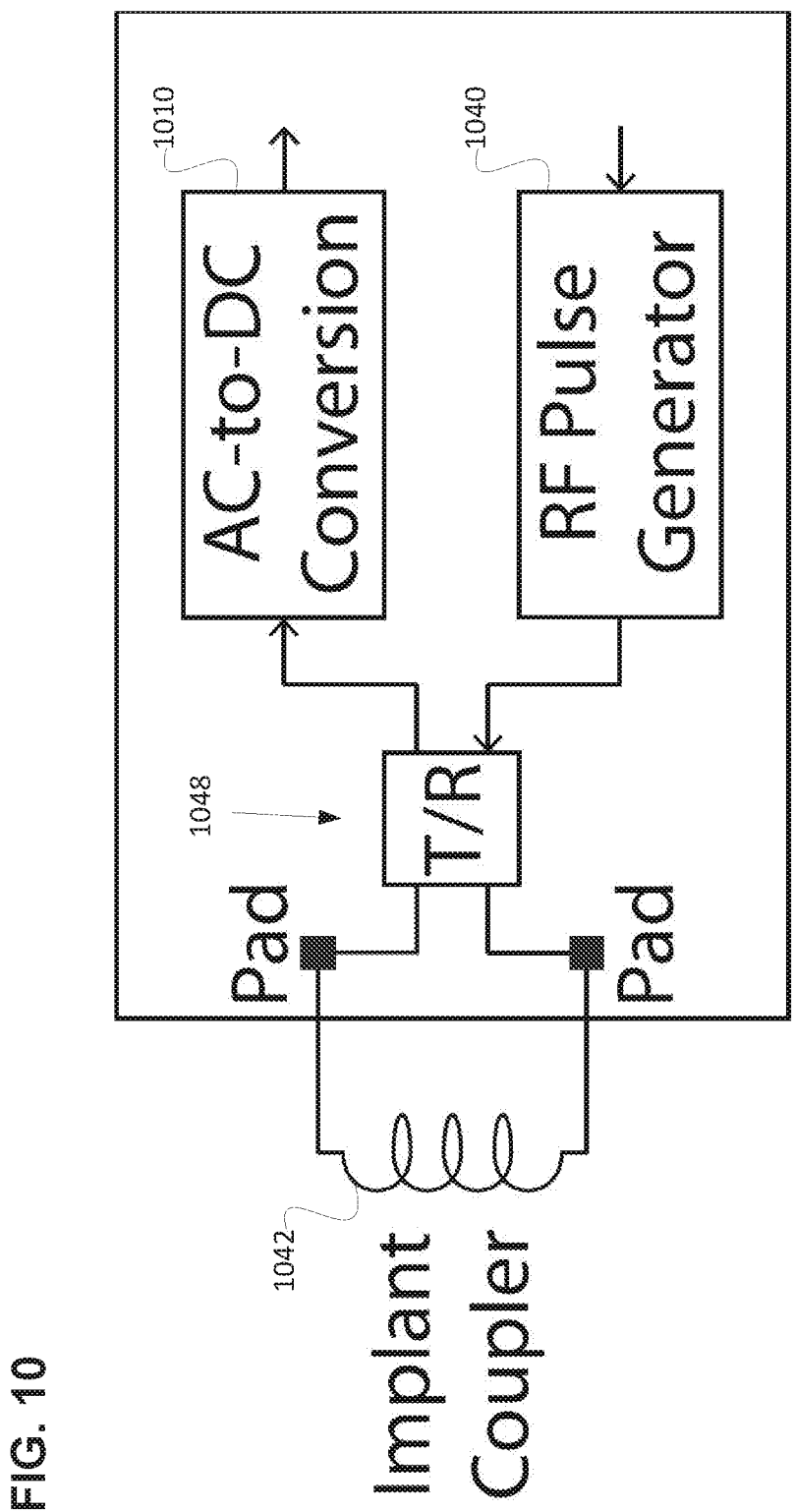
FIG. 10 shows an architecture where the power receiver and data transmitter share the same implant coupler.

The power receiver and data transmitter of FIG. 8 can share the same implant coupler 1042 as shown in FIG. 10. This can be implemented with a transmit-receive switch 1048 (T/R switch), which can connect the AC-DC conversion chain 1010 and the pulse generator 1040 to a single implant coupler 1042.

Figure 11A:
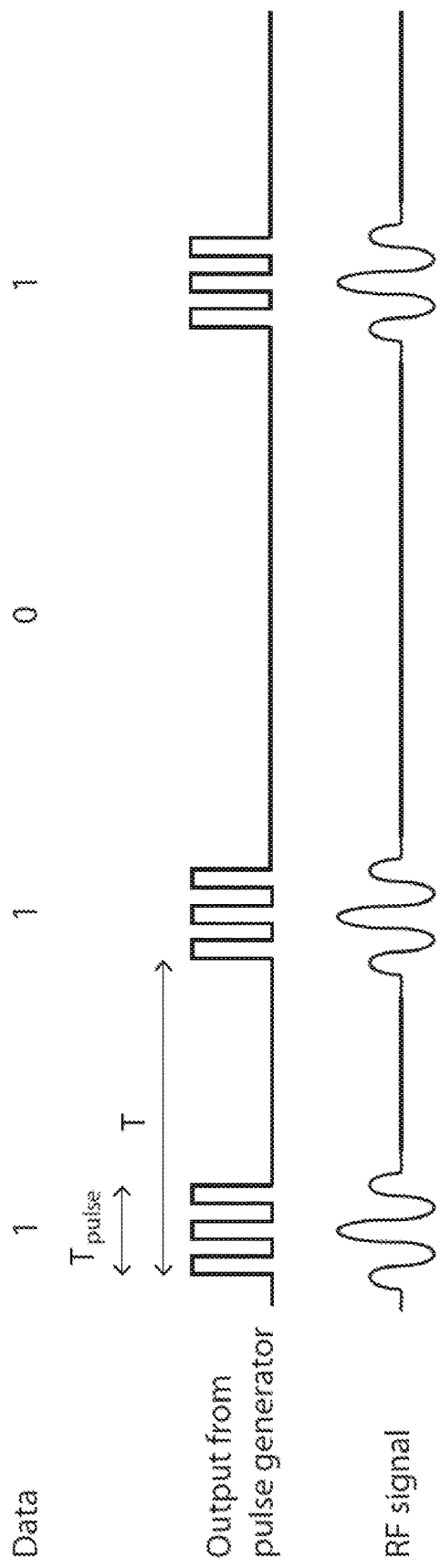
FIGS. 11A-11B illustrate an output sequence of a data transmitter.
Figure 11B:
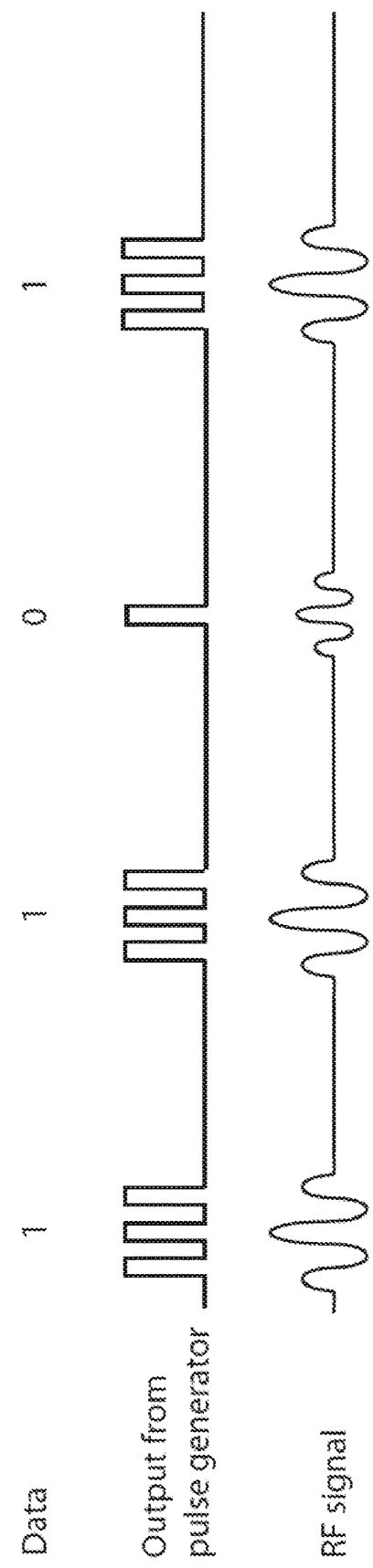

Input to the pulse generator of FIGS. 8-9 can be a sequence of binary symbols, and the output can be a sequence of pulses, as shown in FIGS. 11A-11B. Due to the bandpass filtering, the radio-frequency (RF) signal shown in FIGS. 11A-11B is widened and may have some ringing. Data symbols can be encoded into the RF signal as on-off keying shown in FIG. 11A or amplitude shift keying shown in FIG. 11B.

The pulse width Tpulse can be chosen to be such smaller than the symbol period T such that the peak power (power over the period Tpulse) is much larger than the average power (power over the period T). This will yield a high data rate from a few kbps to 100 Mbps while the average power consumption is low, for example, 10 μW average power with 10 mW peak power. Tissue composition and structure have less impact on the pulsed RF modulation than backscattered modulation. Furthermore, the use of the coupler and the wirebonds as part of the transmitter reduces complexity.

To support simultaneous power delivery and data receiving at the external power transmitting module (e.g., external module 102 from FIG. 1), a vast number of conventional implantable systems use separate frequencies for the power and data carriers, and use separate coupler structures optimized to the respective carriers. The inclusion of two coupler structures increases the size of the external module.

This disclosure provides methods and apparatus to combine the two coupler structures into one, enhancing the compactness of the external module.

Figure 12:
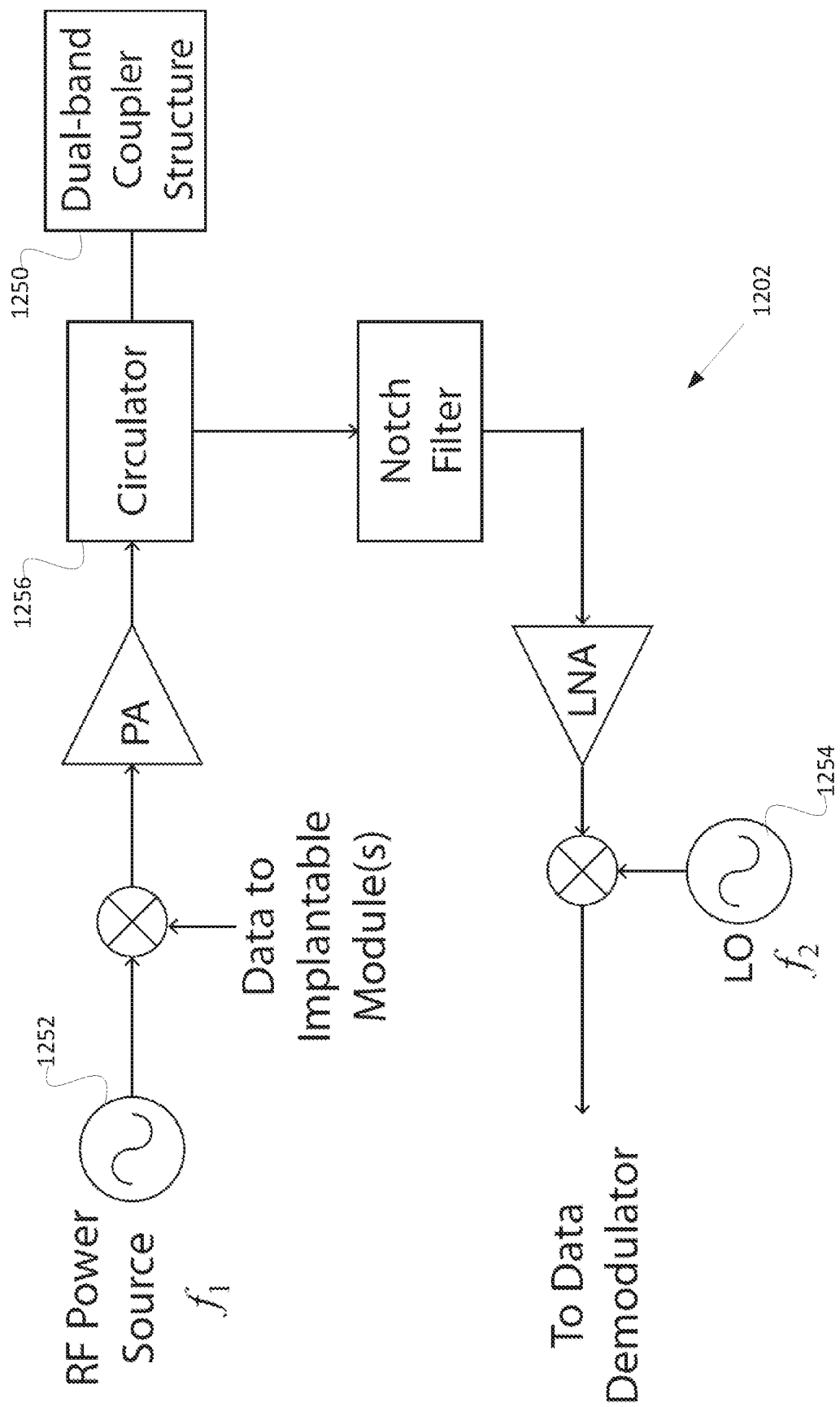
FIG. 12 is a schematic drawing of an external wireless power transmitting module that includes a dual-band coupler structure.

FIG. 12 shows a schematic of the external wireless power transmitting module 1202 having a dual-band coupler structure 1250 to combine two coupler structures into one. The band around frequency f1 from RF power source 1252 can be used to transmit power to the implantable module (e.g., the implantable module of FIG. 1). The dual-band coupler structure can be configured to manipulate evanescent fields outside a patient's tissue to excite/control propagating fields inside a patient's tissue. The band around frequency f2 at LO 1254 can be used to receive data from the implantable module. In one embodiment, the power carrier uses 1.6 GHz while the data carrier uses 2.4 GHz. A circulator 1256 can be included to separate the two signals into two paths. The upper path can be used to transmit power to the implantable module while the lower path can be used to decode data received from the implantable module.

The upper path of FIG. 12 can include an RF power source, a mixer, and a power amplifier (PA). The frequency of the RF power source is $f_1$. The power carrier can also carry data to the implantable module.

The lower path of FIG. 12 can include a notch filter, a low-noise amplifier (LNA), a mixer, a local oscillator, and a data demodulator/decoder. The output frequency of the oscillator is $f_2$. The performance of the circulator in isolating signals to the upper and lower paths is very sensitive to the degree of impedance matching of the coupler to the surrounding tissue medium. It is difficult to achieve perfect matching due to the variability of patient tissue structure and location of the implantable module. A notch filter can be included to reduce the leakage signal from the upper path. The filtered signal can then be amplified by the LNA, and followed by down conversion to baseband signals for data demodulation and decoding. In some embodiments of the invention, the notch filter can be integrated with the LNA, and in another embodiment, the LNA can precede the notch filter.

While the present disclosure is amenable to various modifications and alternative forms, specifics thereof have been shown by way of example in the drawings and will be described in further detail. It should be understood that the intention is not to limit the disclosure to the particular embodiments and/or applications described. Methods of using the embodiments described herein are also included. Various embodiments described above and shown in the figures and attachments may be implemented together and/or in other manners. One or more of the items depicted in the drawings/figures can also be implemented in a more separated or integrated manner, as is useful in accordance with particular applications.

What is claimed is:

1. A wireless power system, comprising:
   an external power transmitting module configured to manipulate evanescent fields outside of tissue to control propagating fields inside the tissue generating a spatially focusing and adaptive steering field inside the tissue; and
   an implantable module configured to receive wireless power from the external power transmitting module via the spatially focusing and adaptive steering field, the implantable module including:
   a coupler configured to induce an alternating current or voltage in the presence of electromagnetic fields or oscillating sound pressure waves;
   a first AC-DC conversion chain configured to rectify the induced alternating current or voltage into a first DC current or voltage in a first energy domain;
   a first DC load coupled to the first AC-DC conversion chain;
   a second AC-DC conversion chain arranged in parallel with the first AC-DC conversion chain and configured to rectify the induced alternating current or voltage into a second DC current or voltage in a second energy domain; and
   a second DC load coupled to the second AC-DC conversion chain.

2. The device of claim 1, wherein the first or second AC-DC conversion chain comprises a rectifier stage.

3. The device of claim 1, wherein the first or second AC-DC conversion chain comprises two or more rectifier stages.

4. The device of claim 1, wherein the first or second AC-DC conversion chain comprises a rectifier stage in series with a DC-DC conversion circuit.

5. The device of claim 1, wherein the first or second AC-DC conversion chain comprises two or more rectifier stages in series with a DC-DC conversion circuit.

6. The device of claim 1, wherein the first or second AC-DC conversion chain comprises a rectifier stage in parallel with a capacitor and a DC-DC conversion circuit, with a battery connected to an output of the DC-DC conversion circuit.

7. The device of claim 1, wherein the first or second AC-DC conversion chain comprises two or more rectifier stages in parallel with a capacitor and a DC-DC conversion circuit, with a battery connected to an output of the DC-DC conversion circuit.

8. The device of claim 1, wherein the first or second AC-DC conversion chain comprises a rectifier stage in series with a DC-DC conversion circuit and a battery.

9. The device of claim 1, wherein the first or second AC-DC conversion chain comprises two or more rectifier stages in series with a DC-DC conversion circuit and a battery.

10. The device of claim 1, wherein the first or second AC-DC conversion chain comprises a rectifier stage in series with a DC-DC conversion circuit, a battery, and a second DC-DC conversion circuit.

11. The device of claim 1, wherein the first or second AC-DC conversion chain comprises two or more rectifier stages in series with a DC-DC conversion circuit, a battery, and a second DC-DC conversion circuit.

12. The device of claim 1, wherein the first DC current or voltage in the first energy domain is optimized for the first DC load.

13. The device of claim 12, wherein the second DC current or voltage in the first energy domain is optimized for the second DC load.

14. The device of claim 13, wherein the first energy domain comprises a low-voltage domain.

15. The device of claim 13, wherein the first DC load comprises sensor circuitry, digital logic, a data transceiver, an analog oscillator, or an analog clock.

16. The device of claim 14, wherein the second energy domain comprises a high-voltage domain.

17. The device of claim 15, wherein the second DC load comprises a battery, a stimulator, or an actuator.

18. The device of claim 1, wherein the external power transmitting module includes one or more sub-wavelength structures configured to manipulate the evanescent fields outside the tissue to generate the spatially focusing and adaptive steering field inside the tissue.

\* \* \* \* \*